United States Patent
Aoki et al.

(10) Patent No.: US 9,851,323 B2
(45) Date of Patent: Dec. 26, 2017

(54) ABNORMALITY DETERMINATION DEVICE OF FUEL PROPERTY SENSOR AND METHOD OF DETERMINING ABNORMALITY OF THE SAME

(71) Applicants: Keiichiro Aoki, Sunto-gun (JP); Kazuhiro Wakao, Susono (JP)

(72) Inventors: Keiichiro Aoki, Sunto-gun (JP); Kazuhiro Wakao, Susono (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 30 days.

(21) Appl. No.: 14/889,230

(22) PCT Filed: May 5, 2014

(86) PCT No.: PCT/IB2014/000664
§ 371 (c)(1),
(2) Date: Nov. 5, 2015

(87) PCT Pub. No.: WO2014/181163
PCT Pub. Date: Nov. 13, 2014

(65) Prior Publication Data
US 2016/0097732 A1 Apr. 7, 2016

(30) Foreign Application Priority Data
May 8, 2013 (JP) .................. 2013-098607

(51) Int. Cl.
*G01N 27/22* (2006.01)
*F02D 41/22* (2006.01)
(Continued)

(52) U.S. Cl.
CPC ......... *G01N 27/22* (2013.01); *F02D 19/0623* (2013.01); *F02D 19/0634* (2013.01);
(Continued)

(58) Field of Classification Search
CPC ..................................................... G01N 27/22
See application file for complete search history.

(56) References Cited

U.S. PATENT DOCUMENTS

2005/0121338 A1* 6/2005 Inoue ...................... C12P 13/02
205/775
2010/0263647 A1 10/2010 Uchida et al.
(Continued)

FOREIGN PATENT DOCUMENTS

EP 2 660 448 A1 11/2013
JP 2009-186339 8/2009
(Continued)

*Primary Examiner* — Jermele M Hollington
*Assistant Examiner* — Feba Pothen
(74) *Attorney, Agent, or Firm* — Finnegan, Henderson, Farabow, Garrett & Dunner, LLP

(57) ABSTRACT

An abnormality determination device is applied to an electrostatic capacitance type fuel property sensor that has a sensing section that senses an electrostatic capacitance of a fuel to be detected. The abnormality determination device of the fuel property sensor acquires a first output that is an output when a predetermined voltage is applied to the sensing section and a second output that is an output when a voltage is not applied to the sensing section. The acquired first output and second output are compared and whether or not the fuel property sensor is abnormal is determined.

4 Claims, 3 Drawing Sheets

(51) Int. Cl.
    *G01N 33/28*     (2006.01)
    *F02D 19/06*     (2006.01)
    *F02D 41/00*     (2006.01)
    *G01N 33/22*     (2006.01)
    *F02D 19/08*     (2006.01)

(52) U.S. Cl.
    CPC ....... *F02D 41/0025* (2013.01); *F02D 41/222* (2013.01); *G01N 27/221* (2013.01); *G01N 33/22* (2013.01); *G01N 33/2852* (2013.01); *F02D 19/084* (2013.01); *F02D 2200/0611* (2013.01); *Y02T 10/36* (2013.01); *Y02T 10/40* (2013.01)

(56) References Cited

U.S. PATENT DOCUMENTS

2010/0264937 A1   10/2010   Tarui et al.
2011/0215813 A1    9/2011   Sasai et al.

FOREIGN PATENT DOCUMENTS

| | | |
|---|---|---|
| JP | 2010-249669 | 11/2010 |
| JP | 2010-256038 | 11/2010 |
| JP | 2011-179459 | 9/2011 |
| WO | WO 2012/090316 A1 | 7/2012 |

\* cited by examiner

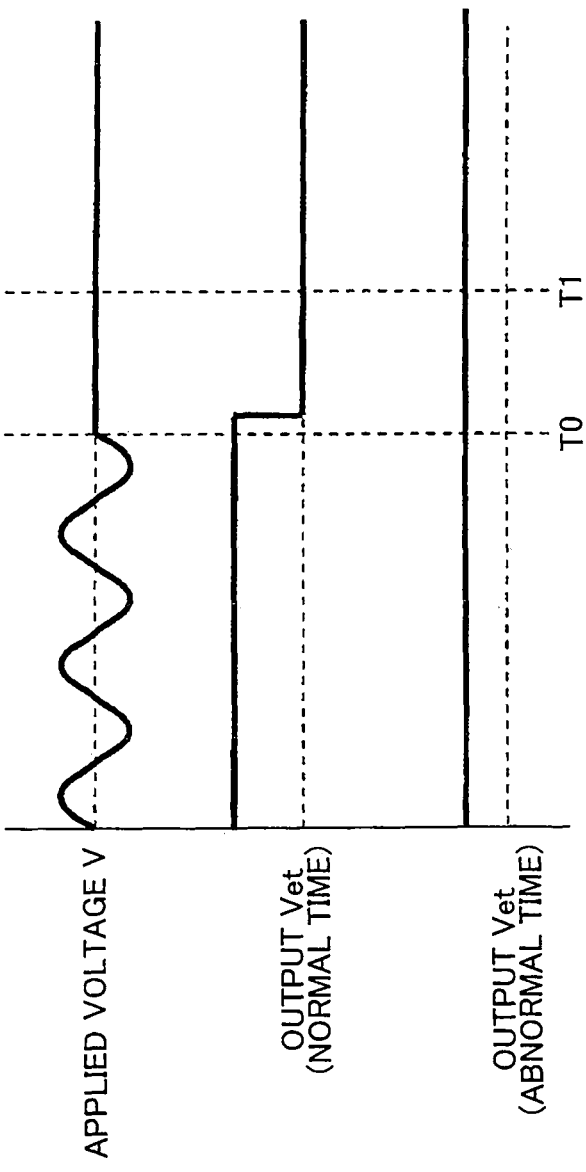

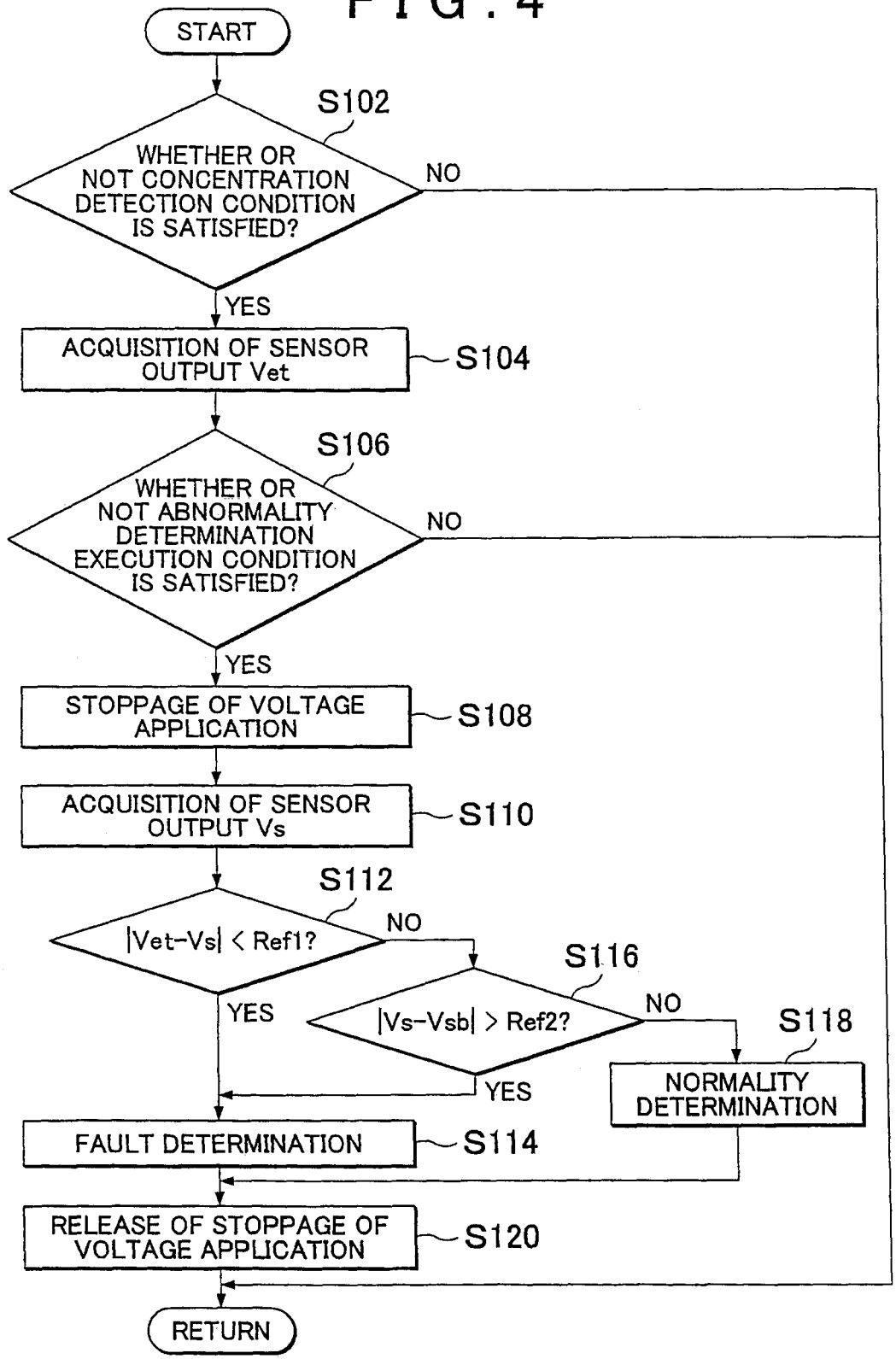

ABNORMALITY DETERMINATION DEVICE OF FUEL PROPERTY SENSOR AND METHOD OF DETERMINING ABNORMALITY OF THE SAME

CROSS-REFERENCE TO RELATED APPLICATIONS

This application is a national phase application of International Application No. PCT/IB2014/000664, filed May 5, 2014, and claims the priority of Japanese Application No. 2013-098607, filed May 8, 2013, the content of both of which is incorporated herein by reference.

BACKGROUND OF THE INVENTION

1. Field of the Invention

The present invention relates to an abnormality determination device of a fuel property sensor, and a method of determining abnormality of the same.

2. Description of Related Art

For example, Japanese Patent Application Publication No. 2010-256038 (JP 2010-256038 A) discloses a technology regarding abnormality determination of an alcohol concentration sensor that is one of fuel property sensors, in particular, a technology that determines presence of stack abnormality where an output of an alcohol concentration sensor shows a constant value and becomes unable to show a change corresponding to the alcohol concentration. In JP 2010-256038 A, a charge period and a discharge period of a detection electrode of the alcohol concentration sensor are switched between two different periods of a first or a second period. As an output of the alcohol concentration sensor, an output corresponding to an electrostatic capacitance of a detection electrode in each of the first and second periods is detected. In JP 2010-256038 A, when a state where a difference between both outputs is not more than a predetermined value continues, the alcohol concentration sensor is determined to be in a state of stack abnormality.

In JP 2010-256038A, when an ON/OFF of a switch is repeated at a plurality of different frequencies, the detection electrode is charged and discharged at different periods. However, when it is required to switch a plurality of frequencies to detect a fault of a fuel property sensor, due to a circuit for carrying out the switching accurately and the like, a cost regarding the fuel property sensor is considered to increase. Further, characteristics of change of the sensor output in accordance with the periods of charge and discharge vary depending on the component of the fuel. Therefore, when the abnormality determination is performed with the plurality of periods, it is necessary to apply adaptation by considering characteristics of every fuel to each of the plurality of periods, and it is considered that man-hours for adaptation increase.

SUMMARY OF THE INVENTION

The present invention was performed to solve the problem as described above, and intends to provide an abnormality determination device of a fuel property sensor, which can determine whether or not abnormality occurs, in which a right value corresponding to a fuel property cannot be output to the fuel property sensor, without switching a frequency of an applied voltage, and an abnormality determination method.

An abnormality determination device of a fuel property sensor having a sensing section configured to sense an electrostatic capacitance of a fuel to be detected, that is a first aspect of the present invention, includes a first acquisition section configured to acquire a first output that is an output of the fuel property sensor in a state where a predetermined voltage is applied to the sensing section, a second acquisition section configured to acquire a second output that is an output of the fuel property sensor in a state where a voltage is not applied to the sensing section, and a determination section configured to determine whether or not the fuel property sensor is abnormal by comparing the first output and the second output.

In the first aspect, the determination section may determine that the fuel property sensor is abnormal when a difference between the first output and the second output is smaller than a first reference value.

In the first aspect, the determination section may further determine whether or not the fuel property sensor is abnormal by comparing the second output and an output of the fuel property sensor when an electrostatic capacitance of the sensing section is zero.

In the first aspect, the determination section may determine that the fuel property sensor is abnormal when a difference between the second output and the output of the fuel property sensor when the electrostatic capacitance of the sensing section is zero is larger than a second reference value.

A method of determining abnormality of a fuel property sensor that is a second aspect of the present invention includes to acquire a first output that is an output of the fuel property sensor in a state where a predetermined voltage is applied to a sensing section of the fuel property sensor that senses an electrostatic capacitance of a fuel to be detected, to acquire a second output that is an output of the fuel property sensor in a state where a voltage is not applied to the sensing section, and to determine whether or not the fuel property sensor is abnormal by comparing the first output and the second output.

According to the first and the second aspect of the present invention, abnormality of the fuel property sensor can be detected by comparing an output when a predetermined voltage is applied to a sensing section of the fuel property sensor and an output when a voltage is not applied. Thus, only by switching an applied state of voltage and a non-applied state of voltage, abnormality of the fuel property sensor can be detected, that is, there is no need of switching a plurality of frequencies of applied voltages to determine abnormality. Therefore, an abnormality determination device can be simplified and the abnormality determination of the fuel property sensor can be performed at a low cost.

BRIEF DESCRIPTION OF THE DRAWINGS

Features, advantages, and technical and industrial significance of exemplary embodiments of the invention will be described below with reference to the accompanying drawings, in which like numerals denote like elements, and wherein:

FIG. 3A, FIG. 3B and FIG. 3C are diagrams for describing an output change between a normal time and an abnormal time of the alcohol concentration sensor in the embodiment of the present invention; and FIG. 4 is a flowchart for describing a control routine executed in the embodiment of the present invention.

DETAILED DESCRIPTION OF EMBODIMENTS

Embodiment

[Entire Structure of System of Embodiment]

Figure 1:
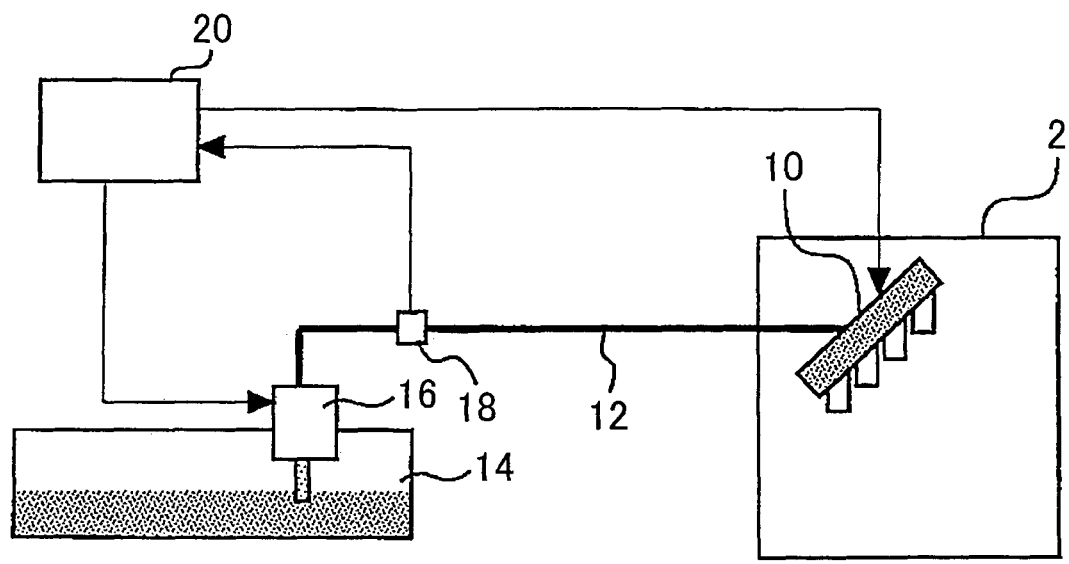
FIG. 1 is a diagram for describing a configuration of an all system including an abnormality determination device of an alcohol concentration sensor in an embodiment of the present invention.

FIG. 1 is a diagram for describing an entire structure of a system including an abnormality determination device of an alcohol concentration sensor in an embodiment of the present invention. In the system of FIG. 1, an internal combustion engine 2 is an internal combustion engine for a FFV (Flexible Fuel Vehicle) capable of using a mixed fuel of alcohol (herein ethanol) and a hydrocarbon-based fuel (herein gasoline).

A fuel injection valve 10 for supplying a fuel is installed in each of cylinders of the internal combustion engine 2. A fuel passage 12 is connected to the fuel injection valve 10. An upper stream side of the fuel passage 12 is connected to a fuel tank 14 for storing a fuel. A fuel pump 16 is installed in the fuel passage 12. On a lower stream of the fuel pump 16 of the fuel passage 12, an alcohol concentration sensor 18 that is one of the fuel property sensors is installed. In the present embodiment, the alcohol concentration sensor 18 is a sensor that generates an output corresponding to an ethanol concentration of a fuel to be detected.

The system of FIG. 1 includes an ECU 20. The ECU 20 is electrically connected to various sensors including the alcohol concentration sensor 18, and takes-in outputs of these sensors. The ECU 20 is electrically connected to actuators such as the fuel pump 16 and the fuel injection valve 10 and processes signals that are taken-in of the various sensors, and, according to a predetermined control program, operates these actuators.

[Structure of Alcohol Concentration Sensor and Concentration Detection]

Figure 2:
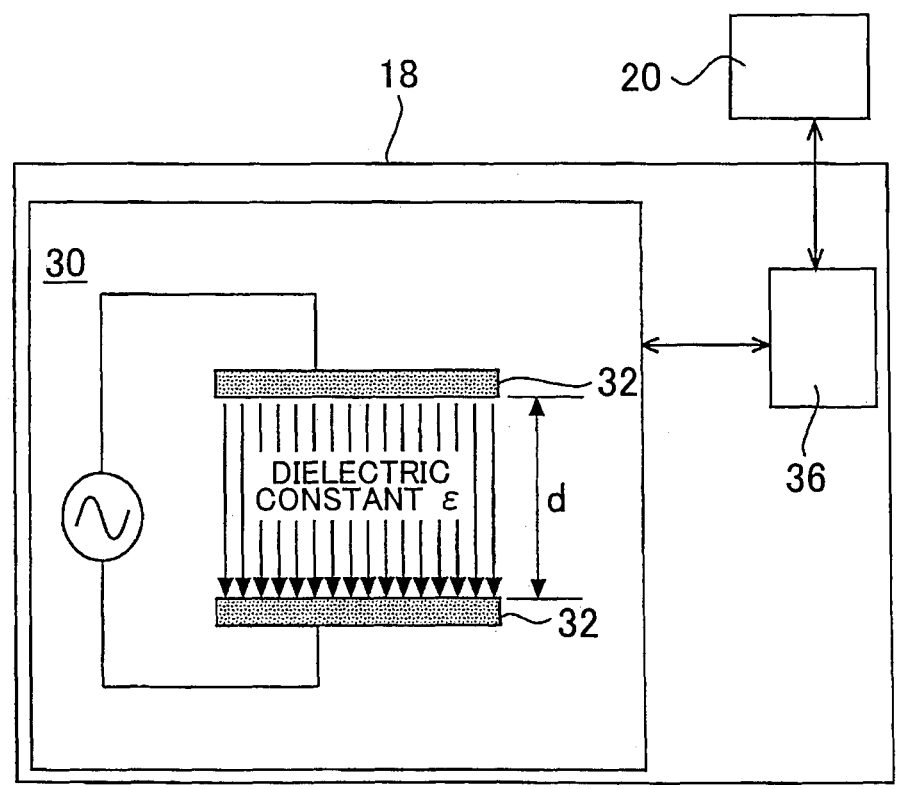
FIG. 2 is a diagram that schematically shows a fundamental structure of an alcohol concentration sensor.

FIG. 2 is a diagram that schematically shows a fundamental structure of the alcohol concentration sensor 18. The alcohol concentration sensor 18 is an electrostatic capacitance type sensor. The alcohol concentration sensor 18 includes a sensing section 30 such as shown in FIG. 2. The sensing section 30 includes a pair of electrodes 32 disposed on opposite positions separated by an inter-electrode distance d. A face that faces with each other of the electrodes 32 has a surface area of S. When the alcohol concentration sensor 18 is installed in the fuel passage 12, the electrodes 32 of the sensing section 30 are disposed inside of the fuel passage 12, and a fuel that flows between the electrodes 32 is a fuel to be detected.

To the pair of electrodes 32, a predetermined AC voltage is applied between the electrodes 32 via a circuit that is not shown in the drawing. An electrostatic capacitance C when a voltage is applied to the pair of electrodes 32 varies in accordance with a dielectric constant $\in$ of the fuel present between the electrodes 32. Specifically, the electrostatic capacitance C between the electrodes 32 can be represented by the following formula (1) with an inter-electrode distance d, a surface area S of the electrodes 32 and a dielectric constant $\in$ of a material (that is, fuel to be detected) between the electrodes 32.

$$\text{Electrostatic capacitance } C = \in \times S/d \qquad (1).$$

Herein, the dielectric constant $\in$ of the fuel is an intrinsic value for every fuel components, and a value that varies in accordance with an ethanol concentration of the fuel. Therefore, on the basis of the electrostatic capacitance C between the electrodes 32, an ethanol concentration of the fuel can be calculated. To the sensing section 30, a not-shown circuit including an operation amplifier and a gain resistance is connected. By the circuit, from the sensing section 30, a voltage corresponding to the electrostatic capacitance C between the electrodes 32 is output as a sensor output Vet.

Now, the alcohol concentration sensor 18 incorporates a microcomputer 36 that functions as an abnormality determination device in the present embodiment. The microcomputer 36 takes-in an output from the sensing section 30 and calculates an alcohol concentration corresponding to the output. Further, the microcomputer 36 switches, by a control signal, a state where an AC voltage is applied between the electrodes 32 of the sensing section 30 and a state where a voltage is not applied. Still further, the microcomputer 36 is electrically connected to the ECU 20, outputs a signal of information regarding the alcohol concentration sensor 18 to the ECU 20, and a signal of information regarding an operation state of the internal combustion engine 2 and the like is input from the ECU 20.

[Abnormality Determination Control of Embodiment]

In the present embodiment, the microcomputer 36 of the alcohol concentration sensor 18 performs an abnormality determination control of the alcohol concentration sensor 18. More specifically, whether or not the so-called stack abnormality where a sensor output of the alcohol concentration sensor 18 is fixed to a constant output and does not change occurs is determined.

FIG. 3A to FIG. 3C are diagrams for describing an abnormality determination control in present embodiment 1, and show output change when the alcohol concentration sensor 18 is normal and abnormal. In FIG. 3A ti FIG. 3C, a horizontal axis expresses a common time. Further, FIG. 3A shows an applied voltage V, FIG. 3B shows a sensor output when the alcohol concentration sensor 18 is normal, and FIG. 3C shows a sensor output when the stack abnormality occurs in the alcohol concentration sensor 18.

In the present embodiment, as shown in FIG. 3A, before a time T0, an applied voltage V that is an AC voltage is applied between the electrodes 32 of the sensing section 30, at the time T0, the applied voltage is stopped, and, after the time T0, the voltage is not applied.

As shown in FIG. 3B, when the alcohol concentration sensor 18 is normal, a sensor output Vet of the sensing section 30 before the time T0 corresponds to an ethanol concentration of the fuel present between the electrodes 32. When application of the applied voltage V is stopped at the time T0, after a response delay time elapsed, the sensor output Vet becomes a voltage Vsb when the voltage application was stopped. A normal sensor output Vsb when the voltage is not applied is an output when the electrostatic capacitance C is zero, that is, a characteristic value for every alcohol concentration sensor 18 that is not influenced by a fuel concentration.

On the other hand, as shown in FIG. 3C, when the stack abnormality occurs in the alcohol concentration sensor 18, regardless of whether the applied voltage V is applied or the voltage application is stopped, the sensor output Vet is fixed to a constant output and does not change.

As described above, in the present embodiment, a first output Vet that is a sensor output in a state where an applied voltage V is applied and a second output Vs that is an output at a predetermined timing T1 after the voltage application is stopped and a predetermined response delay time has elapsed are obtained. Then, when determined to correspond to the following (1), and (2), based on the first output Vet and the second output Vs, it is determined that the stack abnormality occurred in the alcohol concentration sensor 18.

(1) When the sensor output is not different at all or hardly different between when an applied voltage V is applied and after the voltage application is stopped, (2) when the second output Vs when voltage application is stopped is different from the output Vsb when the electrostatic capacitance is zero.

Whether or not correspond to (1) described above is determined by whether or not an absolute value of a difference (Vet−Vs) between the first output Vet and the second output Vs is smaller than a first reference value Ref1. Here, the first reference value Ref1 is optionally set to zero or a value in the neighborhood of the upper limit in a region that is determined to be hardly different between the first and second outputs in the neighborhood of zero. The microcomputer 36 stores the value in advance.

Whether or not corresponds to (2) described above is determined by whether or not an absolute value of a difference (Vs−Vsb) between the second output Vs and the output Vsb when the electrostatic capacitance is zero is larger than a second reference value Ref2. Here, the second reference value Ref2 is optionally set to a value in the neighborhood of the upper limit in a region that is determined that both outputs are different. The microcomputer 36 stores the second reference value Ref2 and a value of the output Vsb when the electrostatic capacitance is zero in advance.

FIG. 4 is a flowchart for describing a control routine that is executed in the embodiment of the present invention. The routine in FIG. 4 is a routine that is repeatedly executed every constant time during an operation of the internal combustion engine 2.

In the routine in FIG. 4, at first, whether or not a concentration detection condition is established is determined (S102). The concentration detection condition is a condition necessary for stably measuring the ethanol concentration of the fuel, optionally set and stored in advance in the microcomputer 36. As the specific concentration detection condition, for example, whether or not the internal combustion engine 2 is after start and after warm-up, whether or not the alcohol concentration sensor 18 is faulty, and whether or not the voltage V is applied during the concentration detection can be cited. When the establishment of the concentration detection condition is not recognized in step S102, the processing this time is stopped once.

In the step S102, when the establishment of the concentration detection condition is recognized, in the next place, in a step S104, the first output Vet is acquired (S104). The first output Vet acquired here is an output when a predetermined voltage is applied, and, when the sensor is normal, an output corresponding to the electrostatic capacitance C of the fuel, that is, an output corresponding to the ethanol concentration of the fuel.

Next, whether or not an abnormality determination execution condition is established is determined (S106). The abnormality determination execution condition is a condition for determining whether or not the present time is a timing where an abnormality determination of the alcohol concentration sensor 18 is necessary and in a state capable of rightly performing an abnormality determination. The abnormality determination execution condition is optionally set in advance and stored in the microcomputer 36. As the specific abnormality determination execution condition, for example, whether or not a time for sufficiently stabilizing the fuel concentration has elapsed after the previous feed, and whether or not a running distance became a fixed distance or more after the previous abnormality determination can be used. When the abnormality determination execution condition is not recognized to be established in Step S106, the processing this time is once stopped.

When the abnormality determination execution condition is recognized to be established in step S106, next, in step S108, voltage application to the sensing section 30 is stopped. Next, at a timing when a fixed time has elapsed after stoppage of voltage application, the second output Vs is detected (S110). Here, the fixed time is set to a time longer than a response delay time until the second output Vs becomes an output at the time of stoppage of voltage application after the stoppage of voltage application and is stored in the microcomputer 36 in advance.

Next, whether or not the difference |Vet−Vs| between the first output Vet and the second output Vs is smaller than the first reference value Ref1 is determined (S112). Here, the first reference value Ref1 is set as shown above and is stored in the microcomputer 36 in advance. When the difference |Vet−Vs| between the first output Vet and the second output Vs is smaller than the first reference value Ref1, that is, |Vet−Vs|<Ref1 is recognized to be established, it is confirmed that an output did not change between during voltage application and after stoppage of voltage application. Therefore, in this time, the processing proceeds to step S114, the alcohol concentration sensor 18 is determined to be abnormal, and a fault determination is issued. Here, the fault determination is stored and a predetermined processing is executed such that a signal of the fault determination is output to the ECU 20 as a signal separate from an ordinary signal of an ethanol concentration.

On the other hand, when |Vet−Vs|<Ref1 is not recognized to be established in step S112, then, the processing proceeds to step S116, and whether or not a difference |Vs−Vsb| between the second output Vs and the output Vsb when the electrostatic capacitance is zero is larger than the second reference value Ref2 is determined. The second reference value Ref2 is a value that is set as shown above and stored in the microcomputer 36 in advance.

When the |Vs−Vsb|>Ref2 is recognized to be established in step S116, irrespective of the stoppage of the voltage application, the output is recognized not to return to the output during the stoppage of voltage application. Therefore, when the |Vs−Vsb|>Ref2 is recognized to be established, the alcohol concentration sensor 18 is determined to be abnormal, and a fault determination is issued in step S114.

On the other hand, when the |Vet−Vs|<Ref1 is not recognized to be established in step S112 and the |Vs−Vsb|>Ref2 is not recognized to be established in step S116, it is recognized that an output changes between during voltage application and during stoppage of voltage application, and an output during stoppage of voltage application shows an output Vsb during the electrostatic capacitance being zero. Therefore, in this case, the processing proceeds to step S118, and the alcohol concentration sensor 18 is determined to be normal.

After the fault determination in step S114 or normality determination in step S118, the stoppage of voltage application is released (S120). Therewith, the abnormality determination control ends, and, when the sensor is normal, the step is returned to a usual mode where the alcohol concentration sensor 18 detects the ethanol concentration of the fuel. Thereafter, the processing this time is stopped once.

As described above, according to the present embodiment, whether or not the stack abnormality of the alcohol concentration sensor 18 is present is determined depending on a difference of the outputs before and after the stoppage of the voltage application. Herein, the electrostatic capacitance of the sensing section 30 of the alcohol concentration sensor 18 is not zero even if an alcohol concentration of the fuel is any concentration between 0% and 100%, when the alcohol concentration sensor 18 is normal, the output during voltage application and the output during voltage stoppage (the case where the electrostatic capacitance is zero) are different. Accordingly, the stack abnormality of the alcohol concentration sensor 18 can be surely detected by comparing the outputs before and after the stoppage of the voltage application as seen from the present embodiment.

In the present embodiment, the abnormality determination can be performed using the output during voltage application and the output after stoppage of voltage application. Therefore, since, for example, a circuit for switching a frequency for abnormality determination becomes unnecessary, a sensor circuit can be simplified. Accordingly, the cost regarding the alcohol concentration sensor 18 can be reduced.

Further, in the present embodiment, the output during voltage application the same as that during usual ethanol concentration detection and the output after stoppage of voltage application are used to perform the abnormality determination. Therefore, in the abnormality determination control, adaptation for every frequencies and components becomes unnecessary, and the abnormality determination can be more simply carried out.

In the present embodiment, a case where the alcohol concentration sensor 18 outputs a voltage corresponding to an electrostatic capacitance C to the microcomputer 36 was described. However, in the present embodiment, the fuel property sensor is not limited thereto, and a value correlating with the electrostatic capacitance C of the sensing section 30 may be used as a sensor output.

Further, in the present embodiment, a case where after acquiring the first output Vet, subsequently the voltage application is stopped, and the abnormality determination is performed was described. However, in the present invention, acquisition of the first output Vet that is used in the abnormality determination and acquisition of the second output Vs during stoppage of voltage application may not continuously be performed. Specifically, for example, the routine of FIG. 4 may be separated between the step S104 and S106. That is, as the first output Vet, a sensor output at an appropriate time in an operation state where a predetermined condition is satisfied may be acquired and stored. Then, when the abnormality determination execution condition is satisfied, the voltage application is stopped, the output Vs during stoppage is acquired, and based on the output Vs and the output Vet already stored, the abnormality determination may be performed. Further, the second output Vs during stoppage of voltage application may be acquired before the first output Vet.

However, in the case where the acquisition of the first output Vet and the acquisition of the second output Vs is separated, at the times of acquisition of both outputs, whether or not other condition that affects on a temperature and other sensor outputs is largely different is desirable to be added as the abnormality determination execution condition. Thus, more accurate abnormality determination can be performed.

Further, in the present embodiment, as the abnormality determination execution condition, whether or not the running distance is a fixed distance or more is cited and described. However, a time interval by which the abnormality determination is performed in the present invention is not limited to the case of the fixed running distance. For example, the abnormality determination in the present invention may be determined to perform every fixed time interval. Further, without limiting to the abnormality determination that is performed every running distance or fixed time interval, for example, one time or a plurality of times of abnormality determination may be performed within one trip from a start to a stop of the internal combustion engine 2.

Still further, in the present embodiment, a case where the abnormality is determined when a difference between the first output Vet and the second output Vs is smaller than the first reference value Ref1 was described. However, in the present invention, the abnormality determination is not limited thereto, as long as the abnormality determination is performed when the first output Vet and the second output Vs are compared and no difference is found between both outputs, the abnormality determination is not limited to one that uses an output difference. Specifically, for example, in the case of a sensor of which output Vsb is not zero at the time where the electrostatic capacitance is zero, based on a ratio of the first output Vet and the second output Vs, the abnormality determination can be performed.

Further, in the present embodiment, a case where as the first output Vet and the second output Vs, outputs as they were measured were used was described. However, in place of theses outputs, an average value of outputs which were detected a plurality of times may be used to perform the abnormality determination. Still furthermore, in the present invention, the alcohol concentration sensor 18 may incorporate a temperature sensor therein and may use a sensor output corrected by the microcomputer 36 according to a temperature sensor output (or temperature). In this case, by means of the sensor output corrected according to a temperature, the abnormality determination can be performed, that is, the abnormality determination can be performed with higher accuracy.

In the present embodiment, a case where the alcohol concentration sensor 18 incorporates the microcomputer 36, and the alcohol concentration sensor 18 itself includes an abnormality determination device was described. However, the present invention is not limited to such case, and an abnormality determination device disposed outside may be connected to the alcohol concentration sensor 18. Further, the abnormality determination of the alcohol concentration sensor 18 may be performed by the ECU 20.

Further, in the present embodiment, a case where at the time of acquisition of the first output Vet, a predetermined AC voltage V is applied to the sensing section 30 was described. However, in the present invention, a voltage applied to acquire the first output Vet, that is, to detect the ethanol concentration is not limited to the AC voltage V. For example, a voltage where an input and a stoppage of a fixed voltage are repeated at a fixed period may be applied.

In the present embodiment, a case where the abnormality of the alcohol concentration sensor is determined was described. However, the present embodiment may be applied to an electrostatic fuel property sensor that issues outputs corresponding to concentrations of other components in the fuel and the abnormality determination of this fuel property sensor may be performed.

In the embodiments described above, when referred to number, numerical quantity, amount, and range of the respective elements, except a case where the number is clearly shown and a case where the number can be clearly and principally specified, the present invention is not limited to the referred number. In addition, a structure and so on described in the present embodiment are not necessarily indispensable in the invention except a case where it is clearly shown and a case where it can be clearly and principally specified.

The invention claimed is:

1. An abnormality determination device of an electrostatic capacitance type fuel property sensor having a sensing section that senses an electrostatic capacitance of a fuel to be detected, comprising:
   a first acquisition section configured to acquire a first output that is an output of the fuel property sensor in a state where a predetermined voltage is applied to the sensing section;
   a second acquisition section configured to acquire a second output that is an output of the fuel property sensor in a state where a voltage is not applied to the sensing section; and
   a determination section configured to determine whether or not an abnormality of the fuel property sensor is present by comparing the first output and the second output.

2. The abnormality determination device of the fuel property sensor according to claim 1, wherein the determination section determines that the fuel property sensor is abnormal when a difference between the first output and the second output is smaller than a first reference value.

3. The abnormality determination device of the fuel property sensor according to claim 1, wherein the determination section further determines whether or not the fuel property sensor is abnormal by comparing the second output and a normal sensor output that corresponds to an output of the fuel property sensor when an electrostatic capacitance of the sensing section is zero.

4. The abnormality determination device of the fuel property sensor according to claim 3, wherein the determination section determines that the fuel property sensor is abnormal when a difference between the second output and the normal sensor output that corresponds to an output of the fuel property sensor when the electrostatic capacitance of the sensing section is zero is larger than a second reference value.

* * * * *